United States Patent [19]

Fujino et al.

[11] 4,315,853
[45] Feb. 16, 1982

[54] POLYPRENYLPEPTIDES AND THEIR PRODUCTION

[75] Inventors: Masahiko Fujino, Takarazuka; Chieko Kitada, Sakai, both of Japan

[73] Assignee: Takeda Chemical Industries, Ltd., Osaka, Japan

[21] Appl. No.: 182,400

[22] Filed: Aug. 26, 1980

[30] Foreign Application Priority Data

Sep. 4, 1979 [JP] Japan .................................. 54-113663

[51] Int. Cl.³ ........................................... C07C 103/52
[52] U.S. Cl. .................................................. 260/112.5 R
[58] Field of Search .................................. 260/112.5 R

[56] References Cited
PUBLICATIONS

AR. Y. Kamiya et al., Agric. Biol. Chem., 42 (1), 209-211, (1978).

AS. Y. Sakagami et al., Agric. Biol. Chem., 42 (6), 1301-1302, (1978).

Primary Examiner—Delbert R. Phillips
Attorney, Agent, or Firm—Wenderoth, Lind & Ponack

[57] ABSTRACT

Novel polyprenylpeptides of the formula

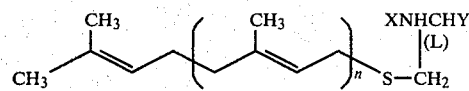

wherein
X is peptide chain of H-Tyr-Pro-Glu-Ile-Ser-Trp-Thr-Arg-Asn-Gly- or H-Glu-His-Asp-Pro-Ser-Ala-Pro-Gly-Asn-Gly-Tyr-; Y is carboxyl which may be amidated or esterified with $C_{1-3}$ alkyl; and n is integer of 3,4 or 5, have the stimulating effect on the mating tube formation of yeast.

9 Claims, No Drawings

POLYPRENYLPEPTIDES AND THEIR PRODUCTION

The present invention relates to novel S-polyprenyl peptides which have the stimulating effect on the mating tube formation of yeast.

It is a well-known, physiological phenomenon of yeasts that *Rhodosporidium toruloides* and *Tremella mesenterica* belonging to Heterobasidiomycetous yeasts go through a life cycle in which a hormone-like substance is secreted during the process of moving from the haploid to the diploid yeast, and is induced by such substance to extend the mating tubes, giving rise to the cell fusion. That such substance is a peptide has become evident from investigation on its active substances. Yet, there is not any physiological action confirmed in the peptides which are supposed to be related in structure to the hormone-like substance, such as simple peptides, e.g., H-Tyr-Pro-Glu-Ile-Ser-Trp-Thr-Arg-Asn-Gly-Cys-OH and H-Glu-His-Asp-Pro-Ser-Ala-Pro-Gly-Asn-Gly-Tyr-Cys-OH. This fact indicates that simple peptides do not exert any action on heterobasidiomycetous yeasts. If there may be obtained a substance exhibiting action on these yeasts, it will not only be able to be utilized effectively for breeding of yeasts, improvement of species, etc., but also to provide an important reagent in the research study on the biochemistry and molecular biochemistry.

The present invention provides novel S-polyprenyl peptides of the general formula:

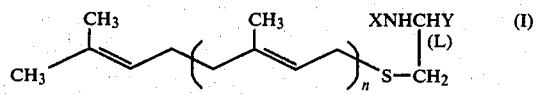

wherein X is a peptide chain of H-Tyr-Pro-Glu-Ile-Ser-Trp-Thr-Arg-Asn-Gly- or H-Glu-His-Asp-Pro-Ser-Ala-Pro-Gly-Asn-Gly-Tyr-; Y is carboxyl which may be amidated or esterified; n is an integer of 3, 4 or 5, which have stronger stimulating effect on the mating tube formation of yeast than naturally occurring ones.

Referring to the above formula (I), Y represents carboxyl which may be amidated (non-substituted amide or alkyl amide with $C_{1-3}$ alkyl such as methyl, ethyl, or propyl) or esterified by $C_{1-3}$ alkyl such as methyl, ethyl or propyl. Among the compound (I), especially preferred are the combination of X being H-Try-Pro-Glu-Ile-Ser-Trp-Thr-Arg-Asn-Gly- and Y being free carboxyl and the combination of X being H-Glu-His-Asp-Pro-Ser-Ala-Pro-Gly-Asn-Gly-Tyr- and Y being carboxyl which is amidated or esterified with $C_{1-3}$ alkyl. Moreover, the former combination is especially effective toward *Rhodosporidium toruloides* and the latter toward *Tremella mesenterica*. In the present specification, to express amino acids or their moieties, peptides, protective groups, reagents used, etc., employed in some instances are the abbreviations adopted by the Commission on the Nomenclature of IUPAC-IUB or those utilized conventionally in the concerned field of science, and as such abbreviations may be mentioned, by way of example, the following:

Ala: Alanine
Arg: Arginine
Asn: Asparagine
Asp: Aspartic acid
Cys: Cysteine
Glu: Glutamic acid
Gly: Glycine
His: Histidine
Ile: Isoleucine
Pro: Proline
Ser: Serine
Thr: Threonine
Trp: Tryptophan
Tyr: Tyrosine
Boc: t-Butoxycarbonyl
Aoc: Amyloxycarbonyl
But: t-Butyl
Z: Benzyloxycarbonyl
Me: Methyl
Bzl: Benzyl
Bzl(Cl): p-Chlorobenzyl
MBzl: p-Methoxybenzyl
Tos: Tosyl
DCC: N,N'-dicyclohexylcarbodiimide
DCHA: Dicyclohexylamine
HONB: N-hydroxy-5-norbornene-2,3-dicarboxyimide
ONB: N-hydroxy-5-norbornene-2,3-dicarboxyimide ester
TFA: Trifluoroacetic acid
DMF: Dimethylformamide Further, the above-mentioned abbreviations for amino acids are directly used to indicate the corresponding residues of amino acids, and the amino acids or their residues, when they are indicated by the above-mentioned abbreviations, shall be construed to mean the L-forms except for glycine.

The compound (I) can be prepared, for example, by the reaction of a cysteine-containing peptide (II) of the formula:

wherein X and Y are as defined above, with a prenyl halide (III) of the formula:

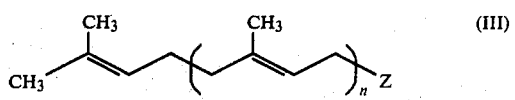

wherein Z is halogen and n is as defined above.

Cysteine-containing peptides for producing the S-polyprenyl peptides are produced, for example, by removing protective groups from the corresponding protected peptides, which are produced by the procedures conventional per se. As to such conventional procedures, detailed descriptions are given in the literature, such as "The Peptide" vol. 1 (1965), by Schröder and Lübke, Academic Press, New York, U.S.A., "Peptide Synthesis", by Izumiya et al., Maruzen Co. (1975), or "Course on Biochemical Experiment I" compiled by Biochemical Society of Japan, "Chemistry of Proteins, Chemical Modification and Peptide Synthesis", published by Tokyo Kagaku Dojin (1977).

Referring briefly below to the method for producing starting peptides, a partial amino acid or peptide capable of constituting the desired polypeptide is allowed to condense with a compound capable of constituting its residual part by the conventional peptide synthesis procedure. As the condensing procedure, there may be mentioned, by way of example, the azide method, chloride method, acid anhydride method, mixed acid anhydride method, DCC method, active ester method, method with the use of the Woodward reagent K, carbodiimidazole method, oxidation-reduction method, DCC-additive method (which utilizes HONB, 1-hydroxybenzotriazole, N-hydroxysuccinimide, etc. as an additive), etc. It is preferable to protect, in advance of conducting said condensation reaction, the carboxyl and amino groups not participating in the reaction as well as hydroxyl and thiol groups by means of the procedure conventional per se, and, with reference to the protecting procedure, carboxyl group may be protected as a tert-alkylamine salt (e.g., with triethylamine, N-methylmorpholine, etc.) or as an ester (e.g., methyl-, ethyl-, benzyl-, p-chlorobenzyl, t-butyl- and t-amyl esters); as the protective group for an amine group there are mentioned, by way of example, benzyloxycarbonyl, t-butoxycarbonyl, iso-bornyloxycarbonyl, etc., while the protective group for an imidazole group of histidine includes, for example, benzyl, tosyl, 2,4-dinitrophenyl, t-butyloxycarbonyl, carbobenzoxyl, etc.; the protective group for the guanidino group of arginine may be exemplified, for example, by nitro, tosyl, carbobenzoxyl, isobornyloxycarbonyl, admantyloxycarbonyl, etc.; and, the protective means for the hydroxyl group of tyrosine and serine is exemplified by ethers having benzyl, t-butyl, t-amyl, etc. as the protective group, and the like, while the protective group means for thiol is exemplified by thioethers having benzyl, p-methoxybenzyl, p-methylbenzyl, t-butyl, etc. as the protective group, and others.

The peptide condensation reaction can be suitably carried out in a solvent normally employed, and employable as such solvent are for example, anhydrous or aqueous dimethylformamide, dimethylsulfoxide, pyridine, chloroform, dioxane, dichloromethane, tetrahydrofuran, ethyl acetate or a suitable mixture thereof. Normally, the reaction is carried out at a temperature within the range of $-20°$ C. to $+60°$ C. The starting compound in the present invention can also be produced easily by the so-called solid-phase synthetic method.

The cysteine-containing peptide thus obtained is subjected to the reaction as a thiol peptide after removing protective group. In order to remove the protective group, catalytic reduction is not preferable, due to the presence of sulfur, but preferred is a method through the acid decomposition reaction with the use of, for example, hydrogen fluoride, methanesulfonic acid, trifluoromethanesulfonic acid, etc. Such reactions are normally conducted in the presence of anisole at a temperature within the range of $-20°$ C. to $+40°$ C. The starting peptide thus produced, after the reaction, can be purified by separatory procedures conventional per se for peptides such as distribution, extraction, reprecipitation, column chromatography, etc.

The procedure of introducing a polyprenyl group into the —SH group of the cysteine-containing peptide of the present invention is conducted by dissolving the starting cysteine-containing peptide, for example, in aqueous diemthylformamide and reacting with polyprenyl halide (e.g., chloride, bromide or iodide, preferably bromide), preferably, in the presence of magnesium oxide, etc. used as a base.

The aqueous dimethylformamide solution normally exhibits a water content of 10 to 70% by volume, preferably 30 to 60% by weight, while the amount of magnesium oxide is used in the molar ratio against the peptide of 1 to 10 equivalents, preferably 2 to 4 equivalents. The polyprenyl halide is in the molar ratio against the peptide of 1 to 10 equivalents, preferably 2 to 4 equivalents in general. The reaction is conducted normally at $-10°$ C. to $60°$ C., preferably at $0°$ C. to $30°$ C., and normally the reaction time is preferably in the range of 3 to 20 hours.

The S-polyprenyl peptides thus produced can be isolated from the reaction mixture by the separation and purification procedures conventional per se (e.g., distribution, extraction, reprecipitation, column chromatography, etc.).

The S-polyprenyl peptide (I) produced by the method of the present invention, exhibiting a mating tube formation stimulating action toward *Rhodosporidium toruloides* at a low concentration of 0.1 to 10 ng/ml and toward *Tremella mesenterica* in concentrations as low as 0.2 to 2 ng/ml, respectively, possesses a strong sexual hormone activity on yeast, and is safe to human being and easy to be handled. Therefore, these S-polyprenyl peptides show a stronger action than the hormone having the similar action being isolated from nature. Based on this, they are of value in the breeding of yeasts, improvement of species, etc., and can also be employed as a reagent for the research studies in the biochemistry and molecular biochemistry. In putting the present compound into use, normally, the present compound may be added to a yeast culture medium to give at least the active concentration as described above, and can also be used as a biochemical reagent by labeling with radioactive iodine or a fluorescent reagent.

Reference examples and examples are given below, whereby the following abbreviations are used for the developing solvent systems for thin layer chromatography.

$Rf_1$ = chloroform:methanol:acetic acid (9:1:0.5)
$Rf_2$ = ethyl acetate:pyridine:acetic acid:water (60:20:6:10)
$Rf_3$ = ethyl acetate:n-butanol:acetic acid:water (1:1:1:1)
$Rf_4$ = n-butanol:pyridine:acetic acid:water (30:20:6:24)

Rf, unless otherwise indicated, is based on using Merck silica gel plate, $60F_{254}$.

REFERENCE EXAMPLE 1

(i) Synthesis of a starting material (a) Production of

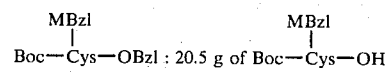

Boc—Cys—OBzl : 20.5 g of Boc—Cys—OH and 9 ml of triethylamine were dissolved in 200 ml of DMF, and the solution was cooled with ice. A solution of 7.2 ml of benzyl bromide in 35 ml of DMF was added dropwise to the solution, followed by stirring while raising gradually its temperature up to room temperature. After 16 hours, insolubles precipitated were filtered out, and the solvent of the filtrate was distilled off under reduced pressure. The residual substance was dissolved in 400 ml of ethyl acetate, washed with a 4% aqueous sodium bicarbonate solution, then with water, and dried over anhydrous sodium sulfate. Ethyl acetate was distilled off, and ether was added to the residual substance, resulting in crystals. The crystals were collected by filtration and recrystallized from ether and petroleum ether.

Yield, 16.1 g; m.p., 61°–64° C.; $[\alpha]_D^{21}$ −45.8° (c 0.53, methanol).

Elementary analysis, for $C_{23}H_{29}O_5NS$: Calcd. C 64.01; H 6.77; N, 3.25; S 7.43, Found C 64.10; H 6.70; N 3.20; S 7.61.

(b) Production of

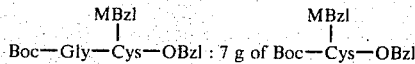

: 7 g of Boc—Cys—OBzl was dissolved in 35 ml of TFA, and the solution was stirred at room temperature for 5 minutes. TFA was distilled off under reduced pressure, and the residual substance was treated with small amounts of ether and petroleum ether to give an oily material. The solvent was removed, and the residue was dissolved in 50 ml of ethyl acetate and neutralized with 2.3 ml of triethylamine. To the solution was added 6 g of Boc-Gly-ONB and stirred for 12 hours. The reaction solution was washed with 0.2 N hydrochloride acid, a 4% aqueous sodium bicarbonate solution and water, and dried over anhydrous sodium sulfate. Distilling off under reduced pressure of the solvent left an oily residue.

Yield, 6.7 g; $Rf_1$ 0.70.

(c) Production of

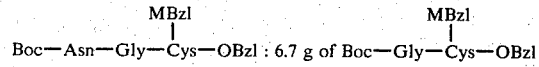

: 6.7 g of Boc—Gly—Cys—OBzl was dissolved in 32.5 ml of TFA, and the solution was stirred at room temperature for 10 minutes. 2.5 ml of a 6.4 N-hydrochloric acid/dioxane solution was added, and the solvent was distilled off under reduced pressure. The residue was washed with petroleum ether containing a small amount of ether, and dissolved in 50 ml of DMF. After cooling with ice, 2.75 ml of triethylamine was added, and the precipitated triethylamine hydrochloride was filtered out. 3.18 g of Boc-Asn-OH and 3.7 g of HONB were added to the filtrate, followed by adding 3.11 g of DCC after cooling down to −5° C. and stirring. After stirring for 16 hours, insoluble precipitate was filtered out, and the filtrate was evaporated to dryness under reduced pressure. The residue was dissolved in 300 ml of ethyl acetate, washed with 0.2 N-hydrochloric acid, a 4% aqueous sodium bicarbonate solution and water, and dried over anhydrous sodium sulfate. The solvent was distilled off under reduced pressure, and the precipitated solid was recovered by filtration with ether.

Yield, 5.7 g. m.p., 121°–123° C. $[\alpha]_D^{23}$ −39.8° (c 0.54, methanol).

Elementary analysis, for $C_{29}H_{38}O_8N_4S$: Calcd., C 57.79; H 6.36; N 9.30; S 5.32. Found, C 58.11; H 6.49; N 9.12; S 5.15. (d) Production of

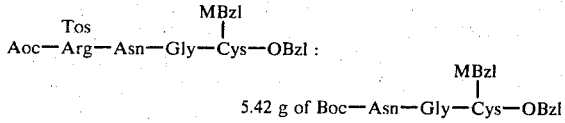

5.42 g of Boc—Asn—Gly—Cys—OBzl was dissolved in 30 ml of TFA, and the solution was stirred at room temperature for 20 minutes. TFA was distilled off under reduced pressure, and 1.5 ml of 6.4 N-hydrochloric acid/dioxane was added to the residue, to which, after stirring, ether was added to recover the resulting precipitate by filtration. The precipitate was dissolved in 50 ml of DMF, and 0.94 ml of triethylamine was added under cooling to neutralize the solution, followed by filtering out the precipitated triethylamine hydrochloride. 2.96 g of

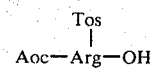

and 2.41 g of HONB were added to the filtrate, and the mixture was cooled to −5° C. to added 1.66 g of DCC. After stirring at room temperature for 16 hours, the precipitate was filtered out, and the solvent was distilled off. The residue was extracted with 300 ml of ethyl acetate, and the extract was washed with 0.2 N-hydrochloric acid, a 4% aqueous sodium bicarbonate solution and water, and dried over anhydrous sodium sulfate. The solvent was distilled off, and the residue was treated with ether to recover by filtration as powder. The product was reprecipitated with acetonitrile and ether.

Yield, 5.52 g, m.p., 70° C. (decomp.), $[\alpha]_D^{23}$ −30.3° (c 0.535, methanol), $Rf_1$, 0.41.

(e) Production of

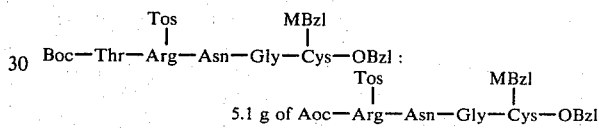

5.1 g of Aoc—Arg—Asn—Gly—Cys—OBzl was dissolved in 35 ml of TFA, and the solution was shaken at room temperature for 15 minutes, followed by evaporating to dryness under reduced pressure and adding 1.6 ml of 6.4 N-hydrochloric acid/dioxane and further ether to recover by filtration as a precipitate. The precipitate was dissolved in 40 ml of DMF to add 0.78 ml of triethylamine for neutralization, and the precipitated triethylamine hydrochloride was filtered out. A dioxane solution of Boc-Thr-ONB synthesized from 1.27 g of Boc-Thr-OH and 1.25 g of HONB was added to the filtrate, and the mixture was stirred for 16 hours. After the reaction, the solvent was distilled off, and the residue was dissolved in 500 ml of ethyl acetate. The solution was washed with 2 N-hydrochloric acid, a 4% aqueous sodium bicarbonate solution and water, and dried over anhydrous sodium sulfate and the solvent was distilled off. The residue, after adding a small amount of ethyl acetate and rubbing with a glass rod, turned into gel-formed crystals. The crystals were recovered by filtration with added ether.

Yield, 5.42 g, m.p., 80°–83° C. (decomp.), $[\alpha]_D^{23}$ −33.0° (c 0.52, methanol), $Rf_1$, 0.20.

(f) Production of

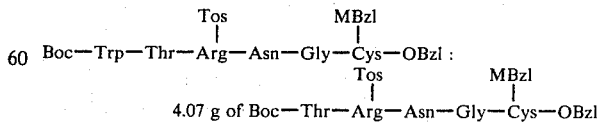

4.07 g of Boc—Thr—Arg—Asn—Gly—Cys—OBzl was dissolved in 25 ml of TFA, and, after leaving the solution at room temperature for 15 minutes, TFA was distilled off under reduced pressure and ether was added to the residue for recovery by filtration. The residue was dissolved in 3 ml of acetonitrile, and 0.8 ml of triethylamine was added for neutralization, followed by adding ether to separate out as a precipitate. The supernatant ether was removed, and the precipitate was dissolved in DMF to cool with ice. To the solution was added Boc-Trp-ONB in dioxane synthesized from 1.28 g of Boc-Trp-OH and 907 mg of HONB, and the mixture was stirred at room temperature for 16 hours. After the reaction, the solvent was distilled off under reduced pressure, and the residue was extracted with 500 ml of ethyl acetate, followed by washing with 0.2 N-hydrochloric acid, a 4% aqueous sodium bicarbonate solution and water and drying over anhydrous sodium sulfate. The solvent was distilled off, and a small amount of ethyl acetate was added to the residue, which turned into gel-formed material. The material was recovered by filtration with a mixed solvent of ethyl acetate and ether. The precipitate thus recovered by filtration was suspended in ethyl acetate, heated up to the boiling point, and recovered by filtration after cooling.

Yield, 3.55 g, m.p., 120° C. (decomp.), $[\alpha]_D^{24}$, $-25.8°$ (c 0.585, methanol), $Rf_1$, 0.18.

(g) Production of

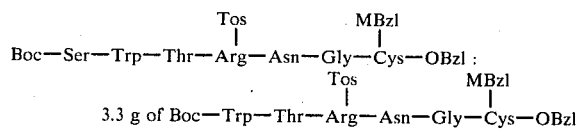

3.3 g of Boc—Trp—Thr—Arg—Asn—Gly—Cys—OBzl was dissolved in 5.5 ml of dioxane containing 20% 1,2-ethanedithiol, and 13 ml of 6.4 N-hydrochloric acid/dioxane was added to allow the solution to stand at room temperature for 35 minutes. The solvent was distilled off, and ether was added to the residue to recover by filtration as powder. The powder was dissolved in 10 ml of DMF to add 0.4 ml of triethylamine for neutralization, and the precipitated triethylamine hydrochloride was filtered out. 621 mg of Boc-Ser-OH and 990 mg of HONB were added to the filtrate, and 749 mg of DCC was added under ice-cooling to stir the mixture. After stirring at room temperature for 16 hours, insolubles were filtered out. The solvent was distilled off under reduced pressure, and ether was added to the residue to recover by filtration as powder. The powder was allowed to flow into a packed silica gel column (5.5 × 12.5 cm) with a solvent of ethyl acetate:pyridine:acetic acid:water (120:10:3:5), and was eluted with the same solvent, whereby the eluted portion of 1490 to 2785 ml was collected, followed by concentrating, adding ether and recovering by filtration the resulting powder.

Yield, 1.9 g, m.p., 150°-153° C. (decomp.), $[\alpha]_D^{25}$, $-28.2°$ (c 0.34, methanol).

Elementary analysis, for $C_{60}H_{78}O_{16}N_{12}S_2$: Calcd., C 55.97; H 6.11; N 13.06; S 4.98. Found, C 55.57; H 6.27; N 12.67; S 4.77.

(h) Production of Boc—Tyr—Pro—OH: 4.4 g of H-Pro-OH was dissolved in 80 ml of aqueous dioxane, and 4.75 ml of triethylamine was added to cool with ice. 11.1 g of Boc-Tyr-ONB was added to the solution, which was stirred vigorously. After distilling off the solvent, the residue was dissolved in 80 ml of a 4% aqueous sodium bicarbonate solution, washed with 50 ml of ether, cooled with ice, and adjusted to pH 2 with 0.2 N hydrochloric acid to thereby extract the separated oily material with 100 ml of ethyl acetate. The ethyl acetate layer was washed with water and dried over anhydrous sodium sulfate to distill off the solvent. The precipitated crystals were recovered by filtration with ether added.

Yield, 4.3 g m.p., 123°-126° C. (decomp.), $[\alpha]_D^{22.5}$, $-23.6°$ (c 0.525, methanol).

Elementary analysis, for $C_{19}H_{26}O_6N_2$: Calcd., C 60.30; H 6.93; N 7.40. Found, C 60.15; H 6.80; N 7.30.

(i) Production of

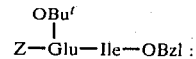

14.2 g of p-toluene sulfonic acid salt of H-Ile-OBzl was suspended in 400 ml of ethyl acetate. The suspension was washed with an aqueous saturated solution of sodium carbonate and then with water, and dried over anhydrous sodium sulfate to distill off the solvent under reduced pressure. Then, 15.6 g of

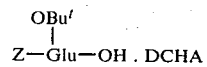

was suspended in 300 ml of ethyl acetate to extract for removal DCHA with 0.2 N sulfuric acid, followed by further washing with water and drying over anhydrous sodium sulfate so as to distill off the solvent under reduced pressure. Both of the residues were dissolved in 140 ml of a mixed solvent of tetrahydrofuran and ethyl acetate (1:1), and 8.1 g of HONB was added. After cooling with ice, 7.44 g of DCC was added and the solution was stirred. After stirring at room temperature for 12 hours, the precipitate was filtered out, and the solvent was distilled off, followed by dissolving the residue in 300 ml of ethyl acetate. The solution was washed with 1 N hydrochloric acid, a 4% aqueous sodium bicarbonate solution and water, and dried over anhydrous sodium sulfate. The solvent was distilled off, and the product crystallized on standing at room temperature. The crystals were recovered by filtration with petroleum ether added.

Yield, 13 g, m.p., 65°-68° C., $[\alpha]_D^{23}$, $-24.5°$ (c 0.60, methanol), $Rf_1$, 0.92.

(j) Production of

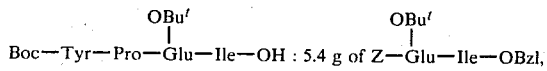

together with 10 ml of N-hydrochloric acid, was dissolved in methanol, and was hydrogenated in the presence of palladium black (1 g). After filtering out palladium black and methanol was evaporated, the resulting residue was dissolved in 100 ml of DMF so as to add 2.8 ml of triethylamine under ice-cooling. On the other hand, 3.78 g of Boc-Tyr-Pro-OH and 2.16 g of HONB were dissolved in 100 ml of a mixed solvent of ethyl acetate and dioxane (1:1), and 2.27 g of DCC was added to the solution to stir at room temperature for 6 hours. The precipitate was filtered off, and the filtrate was added to the DMF solution hereinbefore described to stir for 16 hours. After the reaction, the solvent was distilled off under reduced pressure, and the residue was extracted with 200 ml of water containing 2.5 g of sodium bicarbonate to wash with ether. The water layer was cooled with ice and made acidic with 35 ml of N-hydrochloric acid to extract the separating-out oily material with two 200 ml portions of ethyl acetate.

These portions of ethyl acetate were combined and washed with water, then being dried over anhydrous sodium sulfate. Ethyl acetate was distilled off under reduced pressure, and the residue was treated with ether to recover by filtration as powder. The product, by use of a mixed solvent of chloroform:methanol:acetic acid (107:4:2), was chromatographed on a column of silica gel (5.5×12.5 cm), and elution was conducted with the same solvent system to collect the eluted portion of 680 to 980 ml. The solvent was distilled off, and the residue was treated with ether to recover by filtration as powder.

Yield, 3.45 g, m.p., 115°–119° C. (decomp.), $[\alpha]_D^{23}$, −40.2° (c 0.465, methanol).

Elementary analysis, for $C_{34}H_{52}O_{10}N_4$: Calcd., C 60.34; H 7.74; N 8.28, Found, C 60.22; H 8.02; N 7.82.

(k) Production of

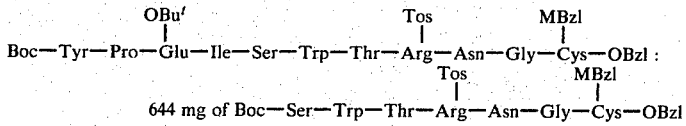

was dissolved in 0.5 ml of DMF and 2 ml of dioxane, and 0.3 ml of 1,2-ethane dithiol and 6 ml of 6.4 N-hydrochloric acid/dioxane were added to the solution to shake at room temperature for 30 minutes. The solvent was distilled off under reduced pressure, and the residue was treated with ether to recover by filtration as powder. The powder was dissolved in 5 ml of DMF, and 0.3 ml of triethylamine was added for neutralization. The precipitated triethylamine hydrochloride was filtered out, and 406 mg of

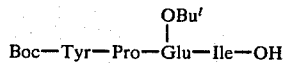

and 360 mg of HONB were added to the filtrate, followed by cooling the mixture down to −10° to −5° C. To this was added 206 mg of DCC and the mixture was stirred for 16 hours. The precipitated insolubles were filtered out, and the solvent was distilled off, followed by treating the residue with acetonitrile and ethyl acetate to recover by filtration as powder.

Yield, 650 mg, m.p., 100°–105° C. (decomp.), $[\alpha]_D^{25}$, −26.6° (c 0.365, methanol).

Elementary analysis, for $C_{89}H_{120}O_{23}N_{16}S_2 \cdot 2H_2O$: Calcd., C 56.79; H 6.64; N 11.91; S 3.41. Found, C 56.23; H 6.67; N 11.67; S 3.90.

Amino acid analysis, Found (Calcd.): Arg 0.99 (1), Asp 1.03(1), Thr 0.98 (1), Ser. 0.92 (1), Glu 0.87 (1), Pro 1.09 (1), Gly 1.0 (1), Cys 0.37 (1), Ile 0.85 (1), Tyr 0.68 (1), average recovery; 72%.

(ii) Production of

H—Tyr—Pro—Glu—Ile—Ser—Trp—Thr—Arg—Asn—Gly—Cys—OH :

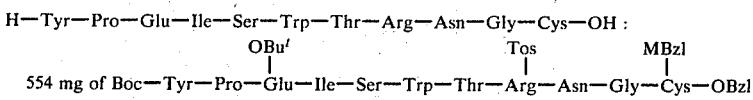

was dissolved in 20 ml of hydrogen fluoride in the presence of 1.6 ml anisole and the solution was stirred at 0° C. for 60 minutes. The hydrogen fluoride was evaporated under reduced pressure, the resulting residue was extracted with 10 ml of water and the extract was washed with 5 ml of ether. The water layer was passed through the Amberlite IRA-410 resin (acetate form) column (1×5 cm) and the resin was washed with water. All the solution was combined and lyophilized to obtain 405 mg, which was chromatographed on Sephadex LH-20 column (2.4×107 cm) and eluted with 0.1 N-acetic acid. The eluted solution 237–281 ml was collected and lyophilized to give 106 mg of SH-peptide.

$[\alpha]_D^{26}$ −63.5° (c 0.60, 1 N-acetic acid), Rf4 (cellulose) 0.64 Amino acid analysis, Found (Calcd.): Arg 1.14(1), Trp 0.59(1), Asp 1.00(1), Thr 1.00(1), Ser 0.95(1), Glu 0.95(1), Pro 1.02(1), Gly 1.00(1), Cys 0.86(1), Ile 0.95(1), Tyr 0.98(1), average recovery 79.1%.

REFERENCE EXAMPLE 2

Production of SH peptided H-Glu-His-Asp-Pro-Ser-Ala-Pro-Gly-Asn-Gly-Tyr-Cys-NH$_2$ and its analog having a methyl ester at the C-terminal thereof:

(i) Synthesis of starting materials (a) Production of

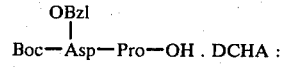

6.9 g of H-Pro-OH, with 8 ml of triethylamine, was dissolved in 70 ml of DMF containing 20% of water, and a dioxane solution of

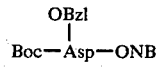

synthesized from 13 g of

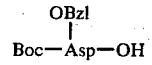

and 8.64 g of HONB was added under cooling, followed by stirring for 12 hours. The reaction solution was concentrated under reduced pressure, and the residue was dissolved by adding an aqueous saturated solution of sodium bicarbonate then washed with ether. The solution was cooled to 0° C. and adjusted to pH 2 to 3 by adding N-hydrochloric acid to extract with two 200 ml portions of ethyl acetate. The ethyl acetate layer was washed with water, and dried over anhydrous sodium sulfate. After distilling off the solvent, the residue was dissolved in 300 ml of ether, and 7.96 ml of DCHA was added to the solution under stirring. The precipitated crystals were recovered by filtration and washed with ether.

Yield, 21 g, m.p., 118°–121° C., $[\alpha]_D^{21}$, −30.3° (c 0.595, methanol).

Elementary analysis, for $C_{33}H_{51}O_7N_3$: Calcd., C 65.86; H 8.54; N 6.96. Found, C 65.89; H 8.59; N 6.84.

(b) Production of

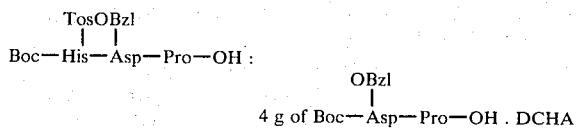

4 g of Boc—Asp—Pro—OH . DCHA $$\text{Boc}-\overset{\overset{\text{OBzl}}{|}}{\text{Asp}}-\text{Pro}-\text{OH}$$

was suspended in 150 ml of ethyl acetate, and the solution was washed with 0.2 N-sulfonic acid and water and dried over anhydrous sodium sulfate. Ethyl acetate was distilled off under reduced pressure, and the residual oily material was dissolved in 15 ml of TFA. After 15 minutes, the solvent was distilled off, and ether was added to the residue to recover by filtration as a gel-formed material. The material was dissolved in 50 ml of DMF and the solution was cooled and to this was added 1.86 ml of triethylamine. A dioxane solution of

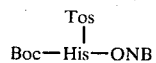

synthesized from 2.86 g of

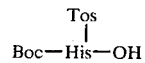

and 1.51 of HONB was added to the solution to stir at room temperature for 16 hours. The reaction mixture was distilled off, and the residue was dissolved in an aqueous saturated solution of sodium bicarbonate, followed by washing with ether and adjusting to pH 2 to 3 with N-hydrochloric acid after cooling with ice. The precipitated oily material was extracted with two 100 ml portions of ethyl acetate, and the ethyl acetate layers were combined to wash with water and dry over anhydrous sodium sulfate. The ethyl acetate was distilled off under reduced pressure, and the residue was treated with ether to recover by filtration as powder. Yield, 2.3 g. The product was a mixture composed of

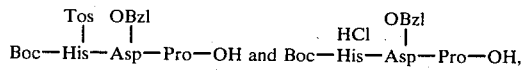

and was therefore used in the following reaction directly without purification.

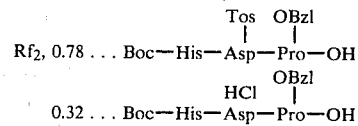

(c) Production of

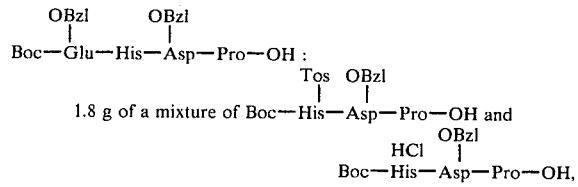

together with 684 mg of 1-hydroxybenzotriazole, was dissolved in 10 ml of tetrahydrofuran and, after stirring for 30 minutes, the tetrahydrofuran was distilled off, and the residue was dissolved in 7 ml of TFA. After 20 minutes, the TFA was distilled off, and the residue was added with ether to recover by filtration as powder. The powder was dissolved in 20 ml of DMF, and 1.06 ml of triethylamine was added to the solution under ice-cooling, followed by adding further a dioxane solution of

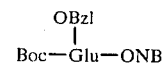

synthesized from 896 mg of

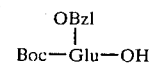

and 573 mg of HONB so as to stir for 16 hours. The solvent was distilled off, and the residue was extracted into an aqueous saturated solution of sodium bicarbonate, followed by washing with ether and ethyl acetate and adding N-hydrochloric acid under ice-cooling to pH 2 to 3. The solution was extracted with two 100 ml portions of ethyl acetate, and the extracts were combined to wash with water and dry over anhydrous sodium sulfate. The solvent was distilled off, and the residue was treated with added ether to recover by filtration as powder, which was reprecipitated from ethyl acetate and ether.

Yield, 1.42 g, m.p., 118°–121° C. (decomp.), $[\alpha]_D^{19}$, −36.8° (c 0.565, methanol), $Rf_2$, 0.42, $Rf_3$, 0.70.

(d) Production of Boc-Ala-Pro-OH: 9.26 g of Boc-Ala-OH and 9.0 g of HONB were dissolved in 50 ml of acetonitrile, and 11 g of DCC was added to the solution under ice-cooling to stir for 4 hours. The resulting urea was filtered out, and the filtrate was evaporated to dryness under reduced pressure. The residue was dissolved in 20 ml of DMF.

On the other hand, 6.9 g of H-Pro-OH was dissolved under heating in 20 ml of DMF and 10 ml of water, and 7 ml of triethylamine was added to the solution to cool with ice. The DMF solution containing the active ester as described above was added to the solution, which was stirred for 6 hours. The DMF was distilled off under reduced pressure, and the residue was dissolved by adding 200 ml of ethyl acetate, followed by washing with an aqueous saturated solution of citric acid and water. The ethyl acetate layer was dried over anhydrous sodium sulfate, and the ethyl acetate was distilled off under reduced pressure. The residue was crystallized with ethyl acetate and petroleum ether, and recovery by filtration yielded 12 g of needle-like crystals. m.p., 150.5–151.5° C.

Elementary analysis, for $C_{13}H_{22}O_5N_2$: Calcd.: C 54.53; H 7.75; N 9.78. Found: C 54.75; H 7.93; N 9.63.

(e) Production of Boc-Ala-Pro-Gly-OBzl(Cl): 5.73 g of Boc-Ala-Pro-OH was dissolved in 40 ml of acetonitrile. After cooling to 0° C., 4 g of HONB and 4.6 g of DCC were added to the solution, which was then stirred for 6 hours. The resulting urea was filtered out, and 7 g of H-Gly-OBzl-(Cl)TFA and 3 ml of triethylamine were added to the filtrate, followed by stirring for 6 hours. The solvent was distilled off under reduced pressure, and the residue was dissolved in 200 ml of ethyl acetate, followed by washing with a 4% aqueous solution of sodium bicarbonate and an aqueous saturated solution of citric acid and drying over anhydrous sodium sulfate to distill off the solvent under reduced pressure. The residue was crystallized with ethyl acetate and petroleum ether, yielding 9.1 g of needle-like crystals. m.p., 108°–110° C., $Rf_1 = 0.77$.

Elementary analysis, for $C_{22}H_{30}O_6N_3Cl$: Calcd.: C 56.46; H 6.46; N 8.98; Cl 7.58. Found: C 56.57; H 6.63; N 8.95; Cl 7.36.

(f) Production of Boc-Ser-Ala-Pro-Gly-OBzl(Cl): 7.02 g of Boc-Ala-Pro-Gly-OBzl(Cl) was dissolved in 30 ml of TFA, and 3 ml of 6 N-hydrochloric acid-dioxane was added to the solution, which was then stirred at 10° C. for 20 minutes. 100 ml of ether was added, and the resulting precipitate was recovered by filtration to wash with ether for drying.

The dried powder was dissolved in 20 ml of DMF, and the solution was cooled to add 2.4 ml of triethylamine.

On the other hand, 3.08 g of Boc-Ser-OH was dissolved in 30 ml of acetonitrile, and 3 g of HONB and 3.3 g of DCC were added to the solution under ice-cooling. After stirring for 4 hours, the resulting urea was filtered out. The filtrate was added to the above-mentioned DMF solution, and the mixture was stirred at room temperature for 10 hours. The solvent was distilled off under reduced pressure, and the residue was dissolved in 100 ml of ethyl acetate to wash with a 4% aqueous solution of sodium bicarbonate and an aqueous saturated solution of citric acid. The solution was evaporated to dryness under reduced pressure, and the residue was dissolved in 10 ml of a 1:8 mixed solution of the solvent system designated by $Rf_2$ and ethyl acetate. The solution was developed over a column of silica gel (6×15 cm, as packed with a 1:8 mixed solution of the solvent designated by $Rf_2$ and ethyl acetate), and the eluted portion of 468 ml to 954 ml was collected to wash with water and evaporate to dryness under reduced pressure. The residue was washed with a 1:1 mixed solution of ether and petroleum ether to recover by filtration to yield 6.8 g.

m.p.: the compound did not indicate the clear melting point but decomposed. $Rf_1 = 0.56$.

Elementary analysis, for $C_{25}H_{35}O_8N_4Cl$: Calcd.: C 54.10; H 6.36; N 9.51; Cl 6.40. Found: C 54.29; H 6.52; N 9.81; Cl 6.16.

(g) Production of Boc-Ser-Ala-Pro-Gly-OH: 1.4 g of Boc-Ser-Ala-Pro-Gly-OBzl(Cl) was dissolved in 50 ml of t-butanol to hydrogenate for 4 hours in the presence of 500 mg of palladium black as a catalyst. The catalyst was filtered out and the filtrate was evaporated to dryness under reduced pressure.

Yield: quantitative, $Rf_1 = 0.08$, $Rf_2 = 0.28$.

(h) Production of

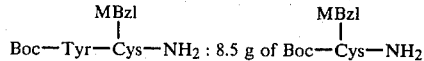

was dissolved in 50 ml of TFA. The solvent was distilled off under reduced pressure 15 minutes later, and to the residue was added ether and petroleum ether. The formed crystals was then collected by filtration. The crystals were dissolved in 50 ml of DMF and, after neutralizing the solution with 4.7 ml of triethylamine, 16.7 g of Boc-Tyr-ONB was added to the solution to stir at room temperature for 16 hours. The solvent was distilled off under reduced pressure, and the residue was dissolved in 250 ml of ethyl acetate, followed by washing with 0.2 N-hydrochloric acid, a 4% aqueous solution of sodium bicarbonate and water, and drying over anhydrous sodium sulfate. The solvent was distilled off and the residue was recovered by filtration from ethyl acetate in the form of gel-formed crystals. Further, the crystals were suspended in ethyl acetate, heated to the boiling point and recovered by filtration after cooling.

Yield, 8.2 g, m.p., 144°–147° C., $[\alpha]_D^{21}$, −24.3° (c 0.61, methanol), $Rf_1$, 0.54.

Elementary analysis, for $C_{25}H_{33}O_6N_3S$: Calcd., C 59.62; H 6.61; N 8.34; S 6.37. Found: C 59.47; H 6.67; N 7.98; S 6.13.

(i) Production of

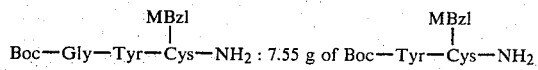

was dissolved in 45 ml of TFA containing 5 ml of anisole and, after allowing the solution to stand at room temperature for 15 minutes, the solvent was distilled off under reduced pressure, followed by recovering by filtration with ether the residue as crystals. The crystals were dissolved in 50 ml of DMF, and, after neutralizing with 2.4 ml of triethylamine being added, 5.2 g Boc-Gly-ONB was added to the solution to stir for 12 hours. The solvent was distilled off and the residue was extracted with 200 ml of ethyl acetate, followed by washing with 0.2 N-hydrochloric acid, a 4% aqueous solution of sodium bicarbonate and water, and drying over anhydrous sodium sulfate. The ethyl acetate was distilled off under reduced pressure, and the residue was recovered by filtration as crystals from ethyl acetate and ether, then being recrystallized from the same solvent system.

Yield, 6.4 g, m.p., 119°–120° C., $[\alpha]_D^{19}$, −32.4° (c 0.515, methanol), $Rf_1$, 0.56.

Elementary analysis, for $C_{27}H_{36}O_7N_4S$: Calcd., C 57.84; H 6.47; N 9.99; S 5.72. Found: C 57.99; H 6.62; N 10.08; S 6.00.

(j) Production of

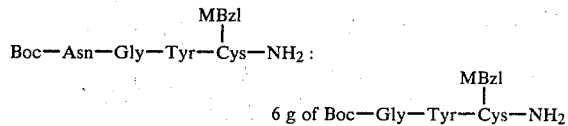

was dissolved in 30 ml of TFA containing 5 ml of anisole. 10 minutes later, the solvent was distilled off under reduced pressure, and the residue was admixed well with 2 ml of 6.4 N-hydrochloric acid/dioxane, followed by adding ether to recover by filtration as powder. The powder was dissolved in 30 ml of DMF, and 1.5 ml of triethylamine was added for neutralization. The precipitated triethylamine hydrochloride was filtered out, and 2.61 g of Boc-Asn-OH and 2.9 g of HONB were added to the filtrate to cool at −5° C. 2.43 g of DCC was added to the mixture under cooling, and stirring was continued for 16 hours. Insolubles were filtered out, and the solvent was distilled off so as to dissolve the resulting residue in 200 ml of ethyl acetate. The solution was washed with 0.2 N-hydrochloric acid, a 4% aqueous solution of sodium bicarbonate and water, and dried over anhydrous sodium sulfate. The solvent was distilled off, and the separating-out gel-formed material was recovered by filtration, suspended in warmed ethyl acetate, and after cooling the material was collected by filtration. After treating with acetonitrile in the same manner, the product was recovered by filtration.

Yield, 3.6 g, m.p., 139°-141° C. (decomp.), $[\alpha]_D^{21}$, −49.3° (c 0.45, methanol), $Rf_1$, 0.33.

Elementary analysis, for $C_{31}H_{42}O_9N_6S$: Calcd., C 55.18; H 6.27; N 12.46; S 4.75. Found, C 54.89; H 6.48; N 12.33; S 4.63.

(k) Production of

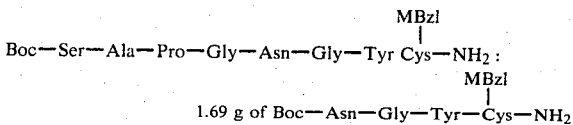

1.69 g of Boc—Asn—Gly—Tyr—Cys(MBzl)—NH$_2$ was dissolved in 7.5 ml of TFA containing 0.8 ml of anisole, and the solution was allowed to stand for 10 minutes. TFA was distilled off under reduced pressure, and the residue was recovered by filtration as powder after triturated with ether. The powder was dissolved in 2 ml of DMF to add 0.7 ml of triethylamine for neutralization, and ether was added to the solution, followed by washing the resulting precipitate with ether and dissolving in 10 ml of DMF. To the solution were added 1.08 g of Boc-Ser-Ala-Pro-Gly-OH and 560 mg of HONB, and the mixture was cooled with ice. 620 mg of DCC was added to the mixture under ice-cooling to stir at room temperature for 16 hours. Insolubles were filtered out, and the solvent was distilled off. The residue, after adding ethyl acetate, was recovered by filtration as powder and washed with acetonitrile, thus yielding 2.35 g of powder. The powder was chromatographed on a column of silica gel (5×15 cm) with a mixture of ethyl acetate:pyridine:acetic acid:water (42:10:3:5), followed by eluting with the same solvent system to collect the eluted portion of 350 to 672 ml. The solvent was distilled off under reduced pressure, and the residue was recovered by filtration as powder by the treatment with ether.

Yield, 1.15 g, m.p., 87°-90° C. (decomp.), $[\alpha]_D^{21}$, −60.2° (c 0.54, methanol), $Rf_2$, 0.42.

(l) Production of

Boc—Glu(OBzl)—His—Asp(OBzl)—Pro—Ser—Ala—Pro—Gly—Asn—Gly—Tyr—Cys(MBzl)—NH$_2$:

494 mg of Boc—Ser—Ala—Pro—Gly—Asn—Gly—Tyr—Cys(MBzl)—NH$_2$ was dissolved in 2 ml of TFA, and 0.1 ml of 6.4 N-hydrochloric acid/dioxane was added to the solution. 15 minutes later, ether was added, and the resulting precipitate was recovered by filtration. The precipitate was dissolved in 3 ml of DMF, and the solution was neutralized with 0.16 ml of triethylamine, followed by filtering out the precipitated triethylamine hydrochloride. The filtrate, after adding 488 mg of Boc—Glu(OBzl)—His—Asp(OBzl)—Pro—OH and 180 mg of HONB to dissolve, was cooled to add further 205 mg of DCC, and stirred for 16 hours. Insolubles were filtered out, and the solvent was distilled off under reduced pressure, followed by adding ethyl acetate to the residue to recover by filtration as powder (830 mg). The powder was developed by silica-gel column (3×29 cm) chromatography with a mixed solvent of ethyl acetate:pyridine:acetic acid:water (60:20:6:10) to collect the eluted portion of 350 to 543 ml. The solvent was distilled off, and ether was added to the residue to recover by filtration as powder.

Yield, 400 mg, m.p., 160°-164° C. (decomp.), $[\alpha]_D^{21}$, −56.8° (c 0.50, methanol), $Rf_2$, 0.23.

Amino acid analysis, Found (Calcd.): His 1.06 (1), Asp 2.00 (2), Ser 0.93 (1), Glu 1.03 (1), Pro 1.98 (2), Gly 1.98 (2), Ala 1.10 (1), Cys 0.41 (1), Tyr 0.45 (1), average recovery, 84.4%.

(m) Production of

Boc—Glu(OBzl)—His—Asp(OBzl)—Pro—Ser—Ala—Pro—Gly—Asn—Gly—Tyr—Cys(MBzl)—OMe : Production of H—Cys(MBzl)—OMe HCl :

50 ml of methanol was cooled at −10° C. and stirred, followed by adding dropwise 13 ml of thionyl chloride and stirring for 10 minutes. 12 g of H—Cys(MBzl)—OH was added to the solution, which was then stirred at room temperature for 16 hours. The crystals separated out were recovered by filtration and washed well with ether to obtain the desired product.

Yield, 12 g, m.p., 152°-153° C., $[\alpha]_D^{23}$, −25.1° (c 0.912, methanol), $Rf_2$, 0.69.

Elementary analysis, for $C_{12}H_{17}O_3NS\cdot HCl$: Calcd., C 49.39; H 6.22; N 4.80; S 10.99; Cl 12.15. Found, C 49.55; H 6.20; N 4.77; S 11.02; Cl 12.23.

(n) Production of

Boc—Glu(OBzl)—His—Asp(OBzl)—Pro—Ser—Ala—Pro—Gly—Asn—Gly—Tyr—Cys(MBzl)—OMe : Using H—Cys(MBzl)—OMe HCl as a starting material, the same procedures as described under the items (h) to (l) were repeated to obtain the desired compound.

Yield, 238 mg, m.p., 120°-124° C. (decomp.), $[\alpha]_D^{21}$, −47.9° (c 0.29, methanol), $Rf_2$, 0.31.

(ii) Production of

H—Glu—His—Asp—Pro—Ser—Ala—Pro—Gly—Asn—Gly—Tyr—Cys—NH$_2$ :

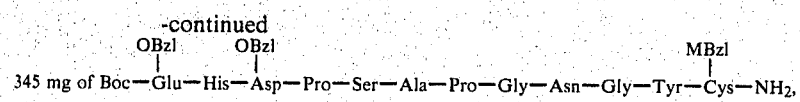

345 mg of Boc—Glu(OBzl)—His—Asp(OBzl)—Pro—Ser—Ala—Pro—Gly—Asn—Gly—Tyr—Cys(MBzl)—NH$_2$, together with 1 ml of anisole, was dissolved in 13 ml of hydrogen fluoride, and the solution was stirred at 0° C. for 60 minutes. The hydrogen fluoride was distilled off under reduced pressure, and the residue was dissolved in 15 ml of water added, followed by washing with two 5 ml portions of ether. The water layer was passed through a column (1×5 cm) of Amberlite IRA-410 (acetate form), and the resin was washed well with water. The eluents were combined for freeze-drying (250 mg). The product was dissolved in 0.1 N acetic acid and developed over a column (2.4×110 cm) of Sephadex LH-20. Elution was conducted with 0.1 N acetic acid, and the eluted portion of 196 to 221 ml was collected and then lyophillized.

Yield, 126 mg, $[\alpha]_D^{24}$, −90.6° (c 0.2, 0.1 N-acetic acid), Rf$_4$ (cellulose), 0.48.

Amino acid analysis, Found (Calcd.): His 0.99 (1), Asp 1.95 (2), Ser 0.96 (1), Glu 0.99 (1), Pro 2.51 (2), Gly 2.0 (2), Ala 1.09 (1), Cys 0.29 (1), Tyr 0.94 (1), average recovery, 61.0%.

(iii) Production of H-Glu-His-Asp-Pro-Ser-Ala-Pro-Gly-Asn-Gly-Tyr-Cys-OMe: In the same manner as described above, the desired SH-peptide was obtained from

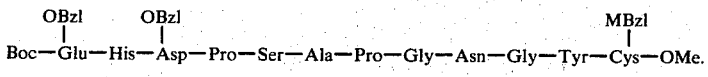

Boc—Glu(OBzl)—His—Asp(OBzl)—Pro—Ser—Ala—Pro—Gly—Asn—Gly—Tyr—Cys(MBzl)—OMe.

$[\alpha]_D^{21}$, −82.9° (c 0.205, 0.1 N-acetic acid), Rf$_4$ (cellulose) 0.44.

Amino acid analysis, Found (Calcd.): His 0.85 (1), Asp 2.02 (2), Ser 0.97 (1), Glu 1.11 (1), Pro 2.17 (2), Gly 2.0 (2), Ala 0.95 (1), Cys 0.95 (1), Tyr 0.97 (1), average recovery (91.7%).

EXAMPLE 1

Production of H-Glu-His-Asp-Pro-Ser-Ala-Pro-Gly-Asn-Gly-Tyr-Cys (S-tetraprenyl)-NH$_2$: 125 mg of H-Glu-His-Asp-Pro-Ser-Ala-Pro-Gly-Asn-Gly-Tyr-Cys-NH$_2$, together with 20 mg of MgO, was dissolved in 4 ml of DMF containing 50% of water, and 1 ml (0.15 mmol) of a solution of tetraprenyl bromide (trans form) in isopropyl ether was added dropwise to the solution, followed by stirring for 16 hours. The solvent was concentrated under reduced pressure, and the residue was dissolved in 0.5 ml of a 60% aqueous methanol solution to develop over a column of (1.4×83.5 cm) of Sephadex LH-20. The eluted portion of 40 to 60 ml was collected and lyophillized, resulting in 66 mg of the product. The product was dissolved in water, and the solution was chromatographed on a column (1×3 cm) of Amberlite XAD-2 to elute with a gradient of water and ethanol. The fraction with an ethanol content of 50 to 85% was collected and lyophylized to obtain 30 mg of the desired product.

Rf$_4$ (cellulose), 0.73.

EXAMPLE 2

Production of H-Glu-His-Asp-Pro-Ser-Ala-Pro-Gly-Asn-Gly-Tyr-Cys (S-pentaprenyl)-NH$_2$: 62 mg of H-Glu-His-Asp-Pro-Ser-Ala-Pro-Gly-Asn-Gly-Tyr-Cys-NH$_2$, together with 10 mg of MgO, was dissolved in 2 ml of aqueous DMF, and 0.5 ml (0.075 mmol) of pentaprenyl bromide (trans form) was added dropwise to the solution, followed by stirring for 16 hours. The solvent was distilled off under reduced pressure, and the residue was dissolved in 0.5 ml of a 60% aqueous methanol solution to develop over Sephadex LH-20 (1.4×83.5 cm). The eluted portion of 60 to 72 ml was collected and lyophilized to obtain 5 mg of the desired product.

Rf$_4$ (cellulose), 0.74.

EXAMPLE 3

Production of H-Glu-His-Asp-Pro-Ser-Ala-Pro-Gly-Asn-Gly-Tyr-Cys (S-pentaprenyl)-OMe: 60 mg of H-Glu-His-Asp-Pro-Ser-Ala-Pro-Gly-Asn-Gly-Tyr-Cys-OMe, together with 10 mg of MgO, was dissolved in 2 ml of aqueous DMF, and 0.5 ml (0.075 mmol) of pentaprenyl bromide (trans form) was added dropwise to the solution, followed by stirring for 16 hours. The solvent was distilled off under reduced pressure, and the residue was dissolved in 0.5 ml of a 60% aqueous methanol solution to develop over Sephadex LH-20 (1.4×83.5 cm). The eluted portion of 62 to 75 ml was collected and lyophilized to obtain 4 mg of the desired product.

Rf$_4$ (cellulose), 0.82

EXAMPLE 4

Production of H-Glu-His-Asp-Pro-Ser-Ala-Pro-Gly-Asn-Gly-Tyr-Cys (S-hexaprenyl)-NH$_2$: 31 mg of H-Glu-His-Asp-Pro-Ser-Ala-Pro-Gly-Asn-Gly-Tyr-Cys-NH$_2$, together with 5 mg of MgO, was dissolved in 3 ml of 70% aqueous DMF, and 0.5 ml (0.04 mmol) of a solution of hexaprenyl bromide (trans form) in isopropyl ether was added dropwise to the solution, followed by stirring for 16 hours. The solvent was distilled off under reduced pressure, and the residue was dissolved in 0.5 ml of a 85% aqueous n-butanol solution to develop over a column (1.4×30 cm) of Sephadex LH-20. The eluted portion of 20 to 30 ml was collected, concentrated and developed again over the same column. The desired fraction was collected, and the solvent was distilled off. The residue was collected to obtain 5 mg of the desired product.

Rf$_4$ (cellulose), 0.76.

EXAMPLE 5

Production of H-Tyr-Pro-Glu-Ile-Ser-Trp-Thr-Arg-Asn-Gly-Cys (S-pentaprenyl)-OH: 40 mg of H-Tyr-Pro-Glu-Ile-Ser-Trp-Thr-Arg-Asn-Gly-Cys-OH, together with 6 mg of MgO, was dissolved in 3 ml of 70% aqueous DMF, and 0.5 ml (0.05 mmol) of a solution of pentaprenyl bromide (trans form) in isopropyl ether was added dropwise to the solution, followed by stirring for 16 hours. The solvent was distilled off under reduced pressure, and the residue was dissolved in 0.5 ml of a 85% aqueous butanol solution to develop over a column (2.3×28.5 cm) of Sephadex LH-20. The fraction of 40 to 56 ml was collected, concentrated and developed again over the same column. The desired fraction was collected, and the solvent was distilled off to obtain 10 mg of the desired product.

Rf₃, 0.70.

Experimental Data

Activity on the mating tube formation of the representatives of S-polyprenyl peptides (I) was assayed in the following way. Cells of a type of *Tremella mesenterica* Fr. (IFO-9313) were cultured in an aqueous medium containing 0.5% Soytone (Difco Laboratories) and glucose at 20° C. for 72 hr. Each of the samples was dissolved in 1 ml of 0.5% Soytone and to this solution were added the cultured a cells ($10^8$–$10^9$/ml) and incubated at 20° C. for 16 hr with reciprocal shaking. After incubation, the number of mating tube formed cells was counted under a microscope and the activity was expressed as the minimum amount of the sample necessary for mating tube formation (>30% of total cells) from a cells. As the reference compound, tremerogen A-10 which is naturally occurring one [Y. Sakagami et al; Agric. Biol. Chem., 42, 1093 (1978)] was used.

The results are summarized in the following table.

TABLE

| Compound | Specific activity (ng/ml) |
| --- | --- |
| Tremerogen A-10 | 1 |
| H—Glu—His—Asp—Pro—Ser—Ala—Pro—Gly—Asn—Gly—Tyr—Cys(S-tetraprenyl)—NH₂ | 0.125 |
| H—Glu—His—Asp—Pro—Ser—Ala—Pro—Gly—Asn—Gly—Tyr—Cys(S-pentaprenyl)—NH₂ | 0.063 |

What is claimed is:

1. A compound of the formula:

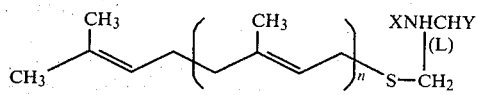

wherein
X is peptide chain of H-Tyr-Pro-Glu-Ile-Ser-Trp-Thr-Arg-Asn-Gly- or H-Glu-His-Asp-Pro-Ser-Ala-Pro-Gly-Asn-Gly-Tyr-; Y is carboxyl which may be amidated or esterified with $C_{1-3}$ alkyl; and n is integer of 3,4 or 5.

2. A compound according to claim 1, wherein X is peptide chain of H-Tyr-Pro-Glu-Ile-Ser-Trp-Thr-Arg-Asn-Gly-.

3. A compound according to claim 1, wherein X is peptide chain of H-Glu-His-Asp-Pro-Ser-Ala-Pro-Gly-Asn-Gly-Tyr-.

4. A compound according to claim 1, wherein n is 4.

5. A compound according to claim 2, wherein Y is free carboxyl.

6. A compound according to claim 3, wherein Y is carboxyl which is amidated or esterified with $C_{1-3}$ alkyl.

7. A compound according to claim 1, said compound being H-Tyr-Pro-Glu-Ile-Ser-Trp-Thr-Arg-Asn-Gly-Cys(S-pentaprenyl)-OH.

8. A compound according to claim 1, said compound being H-Glu-His-Asp-Pro-Ser-Ala-Pro-Gly-Asn-Gly-Tyr-Cys (S-pentaprenyl)-NH₂.

9. A compound according to claim 1, said compound being H-Glu-His-Asp-Pro-Ser-Ala-Pro-Gly-Asn-Gly-Tyr-Cys (S-pentaprenyl)-OCH₃.

* * * * *